United States Patent [19]

Geiselman et al.

[11] Patent Number: 4,844,872
[45] Date of Patent: Jul. 4, 1989

[54] FLUID HANDLING

[75] Inventors: Theodore S. Geiselman, Groveland; James Rasmussen, Plainville, both of Mass.

[73] Assignee: Fisher Scientific Company, Pittsburgh, Pa.

[21] Appl. No.: 74,921

[22] Filed: Jul. 17, 1987

[51] Int. Cl.[4] .................................. G01N 35/06
[52] U.S. Cl. ................... 422/100; 422/63; 422/81; 422/103
[58] Field of Search ............... 422/63–67, 422/81, 100, 103; 137/884, 597, 559; 251/331

[56] References Cited

U.S. PATENT DOCUMENTS

| | | | |
|---|---|---|---|
| 3,951,167 | 4/1976 | Howell | 251/331 |
| 3,963,440 | 6/1976 | Stein | 422/63 |
| 4,108,602 | 8/1978 | Hanson | 422/81 |
| 4,219,530 | 8/1980 | Kopp | 422/81 |
| 4,283,262 | 8/1981 | Cormier . | |
| 4,304,257 | 12/1981 | Webster | 251/331 |
| 4,323,537 | 4/1982 | Mody | 422/65 |
| 4,344,768 | 8/1982 | Packer et al. | 422/100 |
| 4,399,362 | 8/1983 | Cormier . | |
| 4,601,881 | 7/1986 | Webster | 422/67 |
| 4,607,526 | 8/1986 | Bachenheimer et al. | 422/81 |
| 4,624,928 | 11/1986 | Qureshi . | |
| 4,640,821 | 2/1987 | Mody et al. | 422/81 |
| 4,649,028 | 3/1987 | Kaltenbach et al. | 422/100 |
| 4,670,219 | 6/1987 | Nelson et al. | 422/65 |

OTHER PUBLICATIONS

The Henley Group, Inc., *The CELLECT Hematology Systems from Instrumentation Laboratory*, "Systems You Can Count On, All the Time, Every Time".

Primary Examiner—Michael S. Marcus
Assistant Examiner—D. John Griffith, Jr.

[57] ABSTRACT

A liquid handling system includes flow network module structure that defines a contained array of flow channels and a plurality of valves for controlling liquid flow through the flow channel array. The flow network module structure is adapted to be connected to an external source for applying a pressure differential to the flow network array to produce liquid flow within passages of the array. Also incorporated in the flow network module is chamber structure that is connected to the flow channel array and that has port structure in an outer surface of the module structure. Valve structure on the module structure is movable between a first position in which the port structure is closed and a second position in which the port structure is opened, the valve structure including actuator structure for moving a valve member between the first and second positions. Liquid transfer structure, including transport structure and probe structure carried on the transport structure, is adapted to cause movement of the valve structure from its first position to its second position concurrently with the movement of the probe structure into alignment with the chamber port structure for delivery of a quantity of sample material to the sample chamber and subsequent flow through the flow network array for interaction with an auxiliary fluid and transfer to an associated utilization device under the influence of an external pressure source.

16 Claims, 3 Drawing Sheets

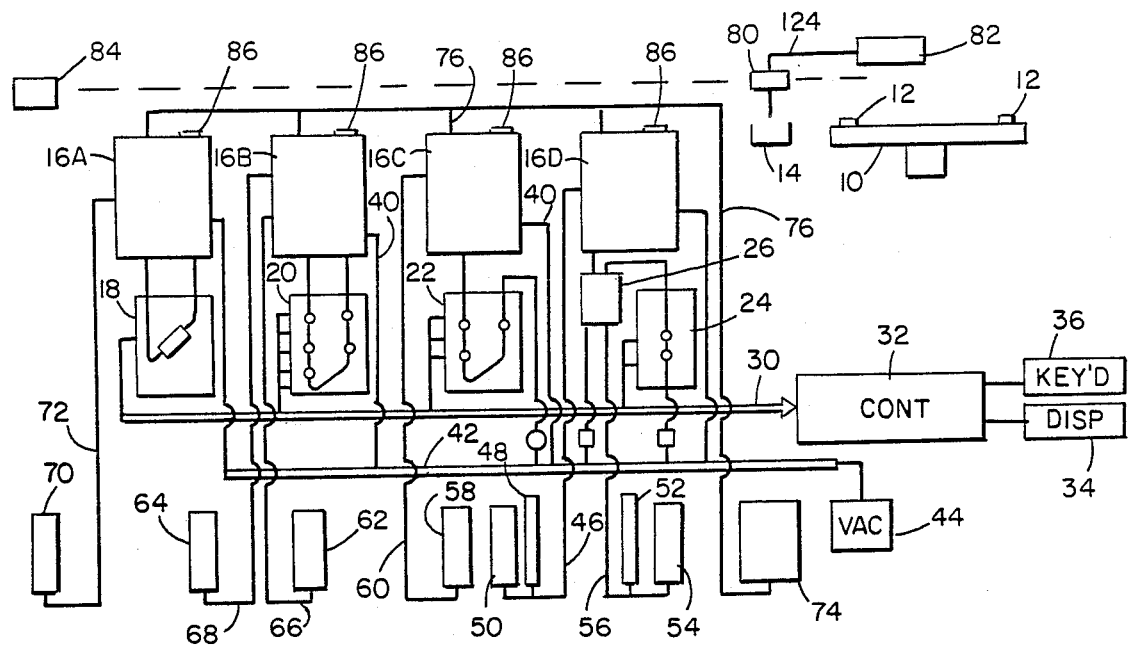
FIG. 1
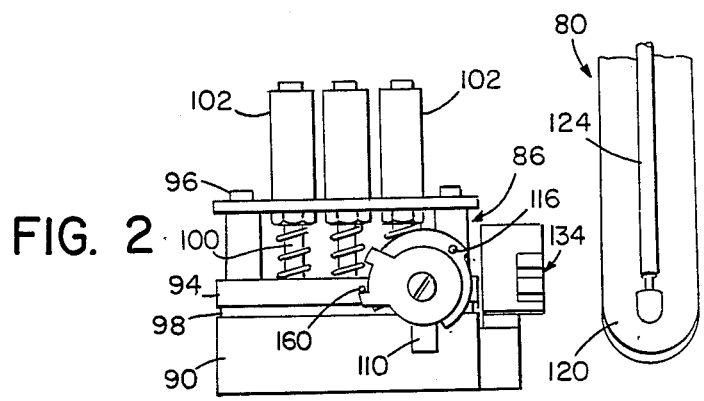
FIG. 2
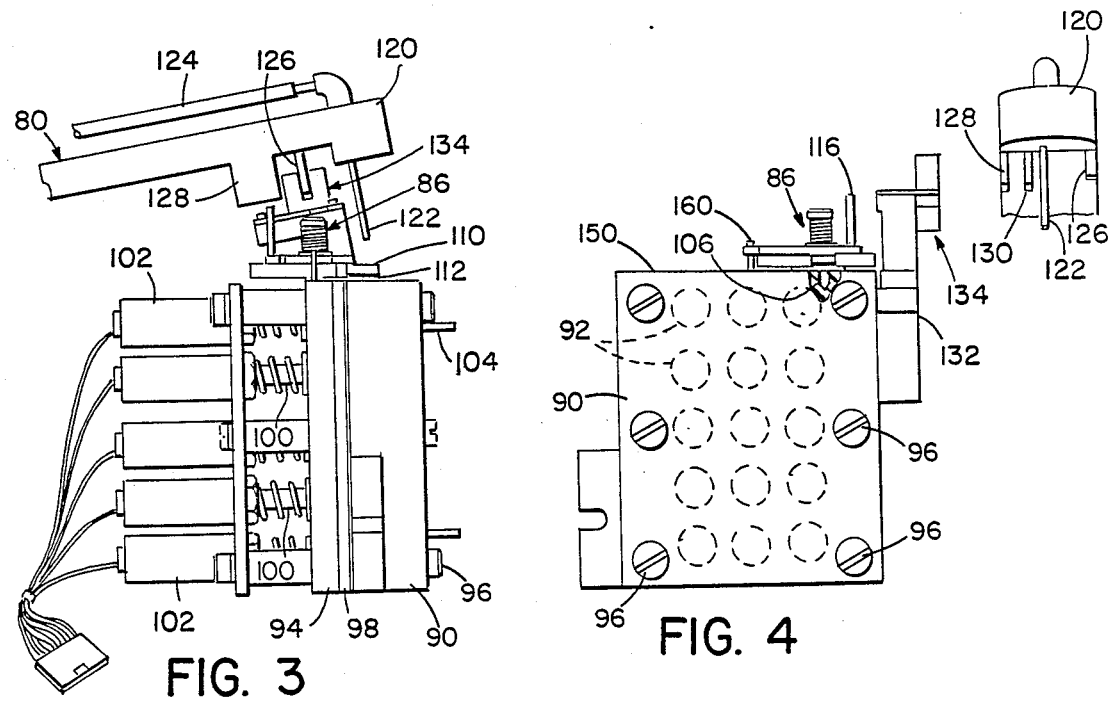
FIG. 3
FIG. 4

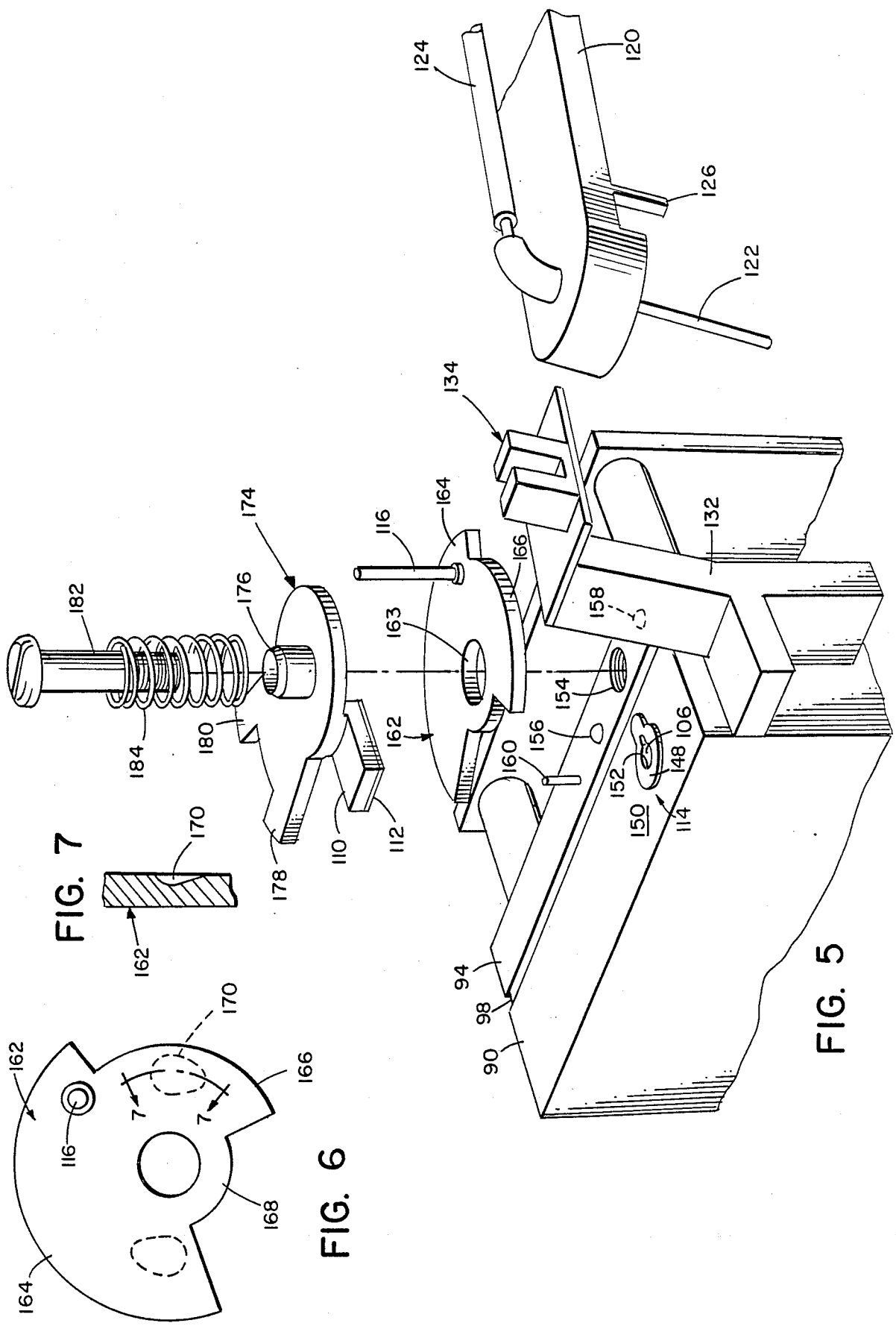

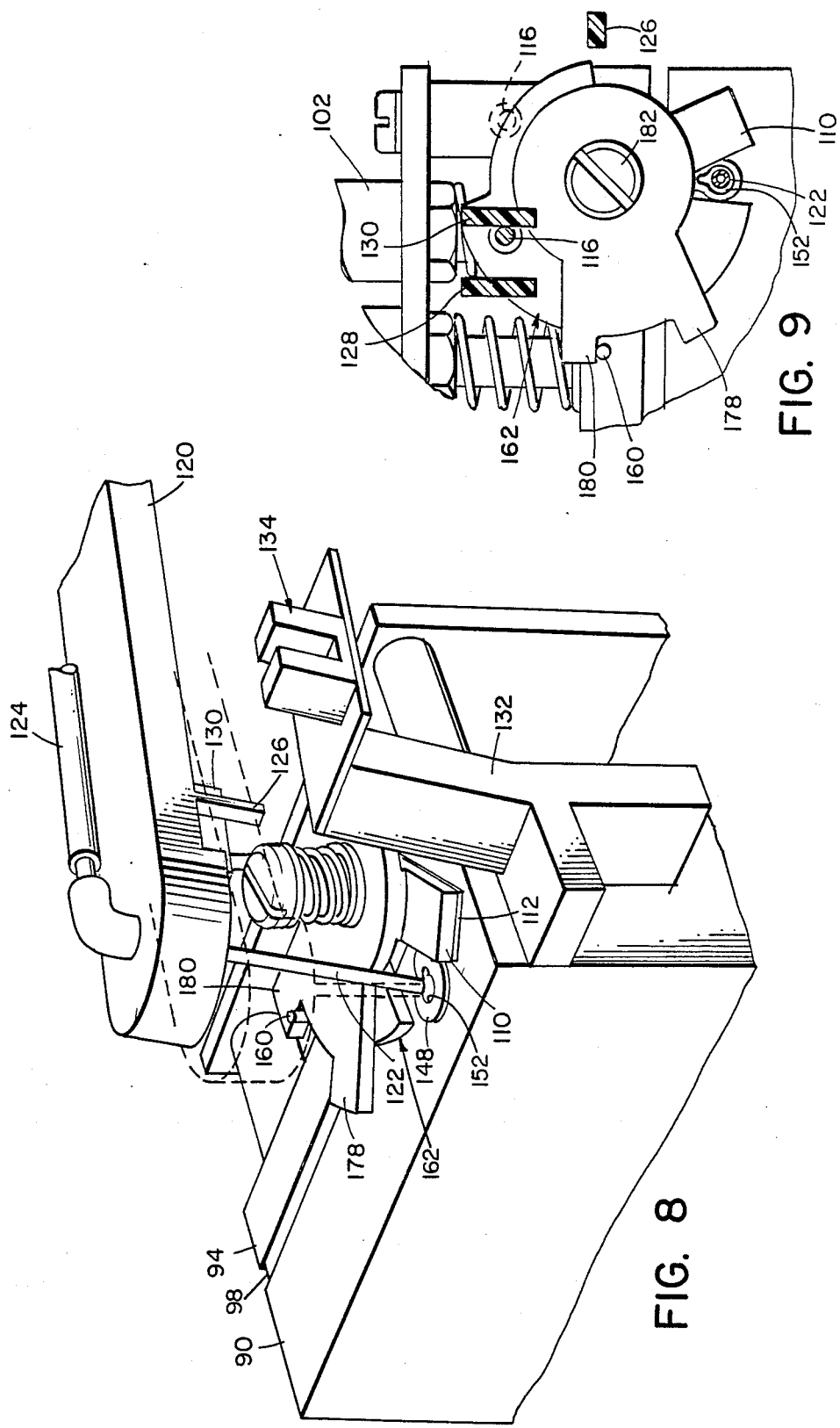

FLUID HANDLING

This invention relates to fluid handling systems, and has particular application to systems for the analysis of constituents of biological liquids and the like.

In the analysis of specific constituents, such as sodium, potassium, glucose, creatinine or carbon dioxide, of biological liquid samples such as whole blood, serum, plasma, or urine, a mixture of the sample liquid to be analyzed and a prechosen reagent or diluent corresponding to one or more of the specific constituents of interest, is disposed in an analysis cell. A variety of arrangements for mixing the sample and reagent or diluent and flowing the resulting mixture to the analysis cell have been proposed. Liquid handling systems for such purposes are shown in Webster U.S. Pat. Nos. 4,304,275 and 4,601,881, for example. In analysis systems of the types shown in those patents, a modular unit with a valve array and interconnecting flow passages has inlet lines for sample reagents, mixing chamber structure and an outlet line that is connected to the analysis cell or other utilization device. The fluids are flowed through the flow network module under the influence of reduced pressures from one or more reduced pressure manifolds which are selectively connected to the flow network by the integrated valve array.

In accordance with one aspect of the invention, there is provided a liquid handling system that includes flow network module structure that defines a contained array of flow channels and a plurality of valves for controlling liquid flow through the flow channel array. The flow network module structure is adapted to be connected to an external source for applying a pressure differential to the flow network array to produce liquid flow within passages of the array. That external source may be the source of enhanced (positive) pressure such as a syringe pump or a source of reduced (negative) pressure such as a vacuum pump and in particular embodiments, sources of both enhanced pressure and reduce pressure are connected to the flow network module for moving fluids through the network. Also incorporated in the flow network module is chamber structure that is connected to the flow channel array and that has port structure in an outer surface of the module structure. Valve structure on the module structure is movable between a first position in which the port structure is closed and a second position in which the port structure is opened, the valve structure including actuator structure for moving a valve member between the first and second positions. Liquid transfer structure, including transport structure and probe structure carried on the transport structure, engages the valve actuator structure adapted to move the valve structure from its first position to its second position concurrently with the movement of the probe structure into alignment with the chamber port structure for delivery of a quantity of sample material to the sample chamber and subsequent flow through the flow network array for interaction with an auxiliary fluid and transfer to an associated utilization device under the influence of an external pressure source.

In a particular embodiment, a plurality of liquid handling systems are incorporated in an analysis system, and each flow network module structure has a corresponding sensor module associated with it. The liquid transfer structure is movable between the several flow network modules and includes mechanical valve actuator mechanism for mechanical engagement with the respective valve actuator structures for moving a valve to open position as the delivery probe is positioned in alignment with the chamber inlet port.

Preferably, the flow network module structure includes a face plate member that has a firm and stable support surface and a flexible sheet member that is clamped in conforming and mating engagement to the firm and stable face plate surface. The sample chamber is preferably in the face plate member and has a volume of less than 100 microliters. A flow channel network is formed in the face plate member, together with valve land portions in one of the engaged surfaces that separates adjacent flow channel portions. Each valve also has an actuator which is arranged to flex the sheet member between a first position in which the surface of the valve sheet member is in mating and sealing engagement with the surface of the face plate member so that the valve land portion blocks flow between adjacent channel portions, and a second position in which the sheet surface is spaced from the first position and allows liquid flow across the land surface between the adjacent channel portions. Each valve has a small volume (less than ten microliters) when opened, and has essentially zero dead space when closed. The gentle and smooth closing action of the valve membrane is in a radially inward direction and the valves provide excellent isolation between the different liquids which are handled by the system.

In a particular embodiment, the sample chamber has a volume of about fifty microliters and the valve structure includes a port closing member that is resiliently biased into seated engagement on an external surface of the module face plate, and a clutch member that carries actuator structure that is engaged by the transport structure and moved to release the clamping pressure on the valve and then move the valve to its open position in coordination with the positioning of the probe in alignment with the opened chamber port.

Other features and advantages will be seen as the following description of a particular embodiment progresses, in conjunction with the drawings, in which:

FIG. 1 is a block diagram of a fluid analysis system in accordance with the invention;

FIG. 2 is a top view of a flow network module unit and sample delivery probe employed in the system of FIG. 1;

FIG. 3 is a side view of the flow network module and delivery probe of FIG. 2;

FIG. 4 is a front view of the flow network module and delivery probe of FIG. 2;

FIG. 5 is an exploded perspective view of a portion of the flow network module and components of the associated valve structure and delivery probe;

FIG. 6 is a plan view of the clutch plate employed in the valve assembly of FIG. 5;

FIG. 7 is a sectional view taken along the line 7—7 of FIG. 6;

FIG. 8 is a perspective view of the probe arm with the valve in open position; and FIG. 9 is a top view of a portion of the flow network module with the valve in open position.

DESCRIPTION OF PARTICULAR EMBODIMENT

Shown in FIG. 1 is a diagrammatic view of a system for analyzing several parameters, such as creatinine, sodium, potassium, glucose, urea, and carbon dioxide of samples of biological fluids such as serum or plasma. The system includes turntable 10 arranged to receive a series of sample cups 12, wash station 14, four flow network modules 16A, 16B, 16C and 16D, and corresponding set of sensor modules 18–24, creatinine module 18 being coupled to flow network module 16A, ion selective electrode (calcium, chloride, potassium, sodium and reference electrode) module 20 being coupled to network module 16B, glucose-urea module 22 being coupled to network module 16C, and pH electrode (total carbon dioxide) module 24 being coupled to network module 16D through gas diffusion module 26. Further details of module 22 may be had with reference to copending application Ser. No. 074,882, entitled Sample Analysis filed concurrently herewith, the disclosure of which is specifically incorporated herein by reference. Output signals from sensor modules 18–24 are applied over lines 30 to controller 32 for analysis and application to an output device such as display 34. Input signals to controller 32 are provided from keyboard 36. Coupled to flow network modules 16 by lines 40 is vacuum manifold 42 in which a vacuum of about nine inches of mercury is maintained by vacuum system 44. Connected to flow network module 16D via line 46 is positive displacement (syringe) pump 48 that supplies reagent from source 50 over line 46 and syringe pump 52 similarly supplies buffer from source 54 over line 56 to gas diffusion module 26. Further details of that flow network module and gas diffusion module may be had with reference to copending application Ser. No. 075,052, entitled Analysis System filed concurrently herewith, the disclosure of which is specifically incorporated herein by reference. Diluent reservoir 58 is connected over line 60 to flow network module 16C; reservoirs 62, 64 of ISE reference and buffer liquids for system are connected over lines 66, 68, respectively, to flow network module 16B; and reservoir 70 of creatinine reagent is connected over line 72 to flow network module 16A. Reservoir 74 of rinse liquid is connected by lines 76 to modules 16A–16C.

A quantity of sample to be analyzed is drawn by syringe pump 82 from sample cup 12 into probe assembly 80 that is translated by drive 84 between sample station cup 12, wash station 14 and the four flow network modules 16. Each flow network module includes valve structure 86 that seals a sample chamber structure port in the flow network module and is moved to open position by the probe assembly 80 for insertion of a sample quantity to be analyzed into the flow network module 16 by operation of pump 82.

Further details of that probe assembly may be had with reference to copending application Ser. No. 074,942, entitled Liquid Handling filed concurrently herewith, the disclosure of which is specifically incorporated herein by reference.

Further details of the flow network modules 16 may be seen with reference to FIGS. 2–4. Each flow network module includes a rectangular face plate member 90 of acrylic resin in which a network of flow passages and valve sites 92 are formed, valve sites 92 being spaced about 1.5 centimeters on center and arranged in five rows and three columns. Clamped against the rear surface of face plate 90 by backing plate 94 and spring loaded fasteners 96 is valve diaphragm membrane sheet 98. Secured to valve diaphragm sheet 98 is an array of valve actuators 100, the head of each actuator being embedded in the valve diaphragm sheet 98 and each actuator being connected to an actuator solenoid 102. Auxiliary fluid lines and reduced pressure lines are connected to the modules 16 by connector tubes 104 that project forward from the front of face plate 90. This manifold array module 16 is of the type shown in Webster U.S. Pat. Nos. 4,304,257 and 4,601,881, the disclosures of which are specifically incorporated herein by reference.

Sample introduction chamber 106 is formed in face plate 90 and mounted on backing plate 94 is a valve assembly 86 that includes valve projection 110 with silicone rubber (35–40 durometer) valve sheet 112 that seats on port structure 114 of chamber 106 to seal that port. Each valve assembly 86 includes an actuator post 116 that is engaged by probe assembly 80 for opening and closing valve 86 in response to movement of probe assembly 80.

Probe assembly 80 includes arm structure 120 that carries stainless steel probe tube 122 (of about one half millimeter inner diameter) that is connected via tubing 124 to metering pump 82. Support arm 120 also includes sensor flag 126 and two spaced depending valve actuator members 128, 130. Mounted on support bracket 132 adjacent the flow network module 16 is sensor assembly 134 which responds to the interposition of sensor flag 126.

Further details of this sample introduction system may be seen with reference to FIG. 5. Sample chamber 106 in face plate 90 has a diameter of about three millimeters and a depth of about seven millimeters. Valving surface 148 projects about one half millimeter above the top surface 150 of face plate 90 and defines sample port 152. Formed in the upper surface of backer plate 94 is threaded recess 154. Also disposed on the upper surface of plate 94 are two hemispherical stainless steel camming members 156, 158, on either side of recess 154, and limit post 160.

Seated on the upper surfaces of camming members 156, 158 is clutch disc 162 that is made of polymeric material and has a thickness of about four millimeters, a major lob portion 164 of about 1.9 centimeters radius, an intermediate lob portion 166 of about 1.5 centimeters radius, and a minor lob portion 168 of about 0.8 centimeter radius. Disc 162 carries actuator post 116. Formed in the lower surface of clutch disc 162 are two cam ramp recesses 170 (FIGS. 6 and 7) that are positioned on the corresponding cam members 156, 158 when the valve 86 is in closed position.

Disposed on clutch disc 162 is valve plate 174 that includes projection 110 on the lower surface of which silicone rubber valve seat 112 is adhered. Valve seat member 112 has a length of about nine millimeters and a width of about six millimeters. Valve plate 174 includes a central guide boss 176 and two locator projections 178, 180. Clutch disc 162 and valve plate 174 are disposed in stacked relation on cam members 156, 158 and secured in position by threaded bolt 182 on which biasing spring 184 is disposed. Bolt 182 extends through boss 176 and aperture 163 and is threaded in recess 154, so that spring 184 imposes a sealing force of about 35 pounds per square inch to seat valve surface 112 against valve surface 150 to seal chamber port 152.

In system operation, transfer assembly 80, after picking up sample from sample cup 12, is moved laterally by stepper motor drive 84 until sensor flag 126 is disposed in sensor assembly 134 and triggers that assembly. In response to that triggering action, drive 84 is slowed and advanced 85 additional steps to position the valve actuator webs 128, 130 on either side of and over valve actuator post 116. Probe arm 120 is then moved downwardly so that the actuator arms 128, 130 bracket post 116 and then arm 120 is moved laterally (100 steps of stepper motor 84) to position probe tube 122 in alignment with chamber port 152 (FIGS. 8 and 9). During that lateral movement, actuator web 130 engages post 116 and rotates clutch disc 162 about the axis of bolt 182. Disc 162 (and valve disc 174) are initially cammed upward along the cam ramp surfaces 170 to lift the valve plate and valve member 112 clear of valve surface 150. As clutch disc 162 is driven further in rotation (about 60°), valve plate 174 is rotated (about 27°) so that arm 180 abuts locator post 160 and positions valve 86 in open position as indicated in FIGS. 8 and 9. In that position, probe tube 122 is aligned with port 152. Probe arm 120 is then moved down to insert probe 122 into chamber 106 and the desired quantity of sample fluid is dispensed by syringe pump 84. After the quantity of sample liquid has been dispensed, the valve operating sequence is reversed with the probe arm 120 being lifted so that the probe 122 clears port 152, then moved laterally to return the valve assembly 86 to its closed position as shown in FIG. 2, and then raised so that the valve actuator webs 128, 130 clear post 116. The transfer assembly 80 may then be returned to the sample tray 10 to pick up a further sample quantity or advanced to deposit specified quantities of sample in other flow network modules of the system.

After the valve 86 is closed, valves in the flow network module 16 are operated to subject flow network channels to pressure from either the positive or negative pressure sources 44, 48, 52 (or both) to flow the sample from the introduction chamber 106 into the flow network for dilution or mixing with reagent, for example, in the manner disclosed in Webster U.S. Pat. No. 4,601,881, and then the diluted or reacted sample material is transferred to the associated sensor module for analysis.

What is claimed is:

1. A liquid handling system comprising
   flow network module structure that includes a contained array of flow channels and a plurality of valves for controlling fluid flow through said flow channel array,
   chamber structure in said module structure connected to said flow channel array, said chamber structure having a port structure in the outer surface of said module structure,
   inlet valve structure on said module structure and movable between a first position in which said port structure is closed and a second position in which said port structure is open,
   liquid transfer structure including transport structure and probe structure carried on said transport structure, said transport structure including actuator structure,
   means responsive to said actuator structure for moving said inlet valve structure to said second position concurrently with the movement of said probe structure into alignment with said chamber port structure,
   means for supplying an auxiliary fluid to said module structure for interaction with sample liquid in said sample chamber,
   means for applying a pressure differential to liquids within said flow network module structure, and
   controller structure for operating valves of said flow network module structure to flow sample liquid and auxiliary liquid through said flow channel array.

2. The system of claim 1 wherein said flow network module structure includes
   a face plate member that has a firm surface, a flexible valve sheet member that has a surface that is softer and more resilient than said face plate surface for mating engagement with said face plate surface,
   a network of channel portions in one of said members with a plurality of valve land portions, each said valve land portion being located between two adjacent ones of said channel portions, the surfaces of said land portions being coincident with the surface of the member in which they are located, and
   a valve control arrangement that includes a plurality of valve actuators, each said actuator being arranged to flex said sheet member between a first position in which said valve sheet surface is in mating and sealing engagement with said surface of said valve face plate to sealingly block flow between adjacent ones of channel portions, and the second position in which said sheet surface is spaced away from said first position to allow flow through between said adjacent channel portions across the land portion corresponding to that actuator.

3. The system of claim 2 wherein said sample chamber port structure is in a face plate member surface that is generally perpendicular to said firm face plate surface.

4. The system of claim 1 wherein said inlet valve structure includes a valve member that is movable by said transport structure to move said valve member from said first position in alignment with said chamber port to said second position so that said probe structure may dispense fluid into said chamber structure.

5. The system of claim 4 wherein said inlet valve structure further includes clutch structure for initially raising said valve member and then moving said valve member from said first position to said second position.

6. The system of claim 5 wherein said flow network module structure includes a face plate member, and said clutch structure and said face plate structure include cooperating camming surfaces.

7. The system of claim 1 wherein said chamber structure has a volume of less than one hundred microliters.

8. The system of claim 7 wherein said flow network module structure includes a face plate member, and said sample chamber port structure is in a surface of said face plate member.

9. The system of claim 8 and further including cam structure on said flow network module structure, and wherein said inlet valve structure includes a valve member, a clutch disc and biasing means, said valve member and said clutch disc being disposed in stacked relation and biased against said cam structure by said biasing means, said clutch member being movable by said transport structure to initially raise said valve member against the biasing force of said biasing means and then move said valve member from said first position in alignment with said chamber port to said second position so that said probe structure may dispense fluid into said chamber structure.

10. The system of claim 1 and further including sensor structure adjacent said valve structure, and sensor means carried by said transport structure, said sensor structure and said sensor means cooperating to indicate movement of said probe structure into a position adjacent said chamber port structure.

11. The system of claim 1 wherein said inlet valve structure includes upstanding post structure and said actuator structure includes depending structure for engagement with said post structure for moving said inlet valve structure between said first and second positions.

12. The system of claim 11 and further including cam structure on said flow network module structure, and wherein said inlet valve structure includes a valve member, a clutch disc and biasing means, said valve member and said clutch disc being disposed in stacked relation and biased against said cam structure by said biasing means, said clutch member being movable by said transport structure to initially raise said valve member against the biasing force of said biasing means and then move said valve member from said first position in alignment with said chamber port to said second position so that said probe structure may dispense fluid into said chamber structure.

13. The system of claim 12 and further including sensor structure adjacent said inlet valve structure, and sensor means carried by said transport structure, said sensor structure and said sensor means cooperating to indicate movement of said probe structure into a position adjacent said chamber port structure.

14. The system of claim 13 wherein said chamber structure has a volume of less than one hundred microliters.

15. The system of claim 14 wherein said flow network module structure includes
- a face plate member that has a firm surface, a flexible valve sheet member that has a surface that is softer and more resilient than said face plate surface for mating engagement with said face plate surface,
- a network of channel portions in one of said members with a plurality of valve land portions, each said valve land portion being located between two adjacent ones of said channel portions, the surfaces of said land portions being coincident with the surface of the member in which they are located, and
- a valve control arrangement includes a plurality of valve actuators, each said actuator being arranged to flex said sheet member between a first position in which said valve sheet surface is in mating and sealing engagement with said surface of said valve face plate to sealingly block flow between adjacent ones of channel portions, and the second position in which said sheet surface is spaced away from said first position to allow flow through between said adjacent channel portions across the land portion corresponding to that actuator.

16. The system of claim 15 wherein said sample chamber port structure is in a face plate member surface that is generally perpendicular to said firm surface of said face plate.

* * * * *